(12) United States Patent
Liu et al.

(10) Patent No.: US 11,453,915 B2
(45) Date of Patent: Sep. 27, 2022

(54) MIRNA MARKER AND KIT ASSOCIATED WITH POSTMENOPAUSAL OSTEOPOROSIS

(71) Applicant: Wuhan University, Wuhan (CN)

(72) Inventors: Huan Liu, Wuhan (CN); Chujiao Lin, Wuhan (CN); Zhi Chen, Wuhan (CN)

(73) Assignee: Wuhan University, Hubei (CN)

( * ) Notice: Subject to any disclaimer, the term of this patent is extended or adjusted under 35 U.S.C. 154(b) by 220 days.

(21) Appl. No.: 16/617,370

(22) PCT Filed: Sep. 1, 2017

(86) PCT No.: PCT/CN2017/100135
§ 371 (c)(1),
(2) Date: Nov. 26, 2019

(87) PCT Pub. No.: WO2019/033468
PCT Pub. Date: Feb. 21, 2019

(65) Prior Publication Data
US 2021/0123101 A1    Apr. 29, 2021

(30) Foreign Application Priority Data
Aug. 17, 2017 (CN) .......................... 201710708188.9

(51) Int. Cl.
*C12N 15/11* (2006.01)
*C12Q 1/6883* (2018.01)
*C12N 15/63* (2006.01)

(52) U.S. Cl.
CPC .......... *C12Q 1/6883* (2013.01); *C12N 15/11* (2013.01); *C12N 15/63* (2013.01); *C12Q 2600/158* (2013.01); *C12Q 2600/178* (2013.01)

(58) Field of Classification Search
CPC .................... C12N 15/11; C12Q 2600/178
See application file for complete search history.

(56) References Cited

U.S. PATENT DOCUMENTS

2014/0363469 A1* 12/2014 Meyers ................ A61K 39/245
424/231.1

FOREIGN PATENT DOCUMENTS

WO    WO-2013063544 A1 *  5/2013 ........... C12Q 1/6886

* cited by examiner

*Primary Examiner* — Ekaterina Poliakova-Georgantas
(74) *Attorney, Agent, or Firm* — Umberg Zipser LLP; Jason Tejani (57) ABSTRACT

Provided in the present invention is the use of the miR-338 cluster as a marker of postmenopausal osteoporosis. In the present invention, it was found that the miR-338 cluster such as miR-338-3p and/or miR-3065-5p are highly expressed in patients with postmenopausal osteoporosis, and it can be used as a marker of postmenopausal osteoporosis, used for preparing an auxiliary diagnostic kit for postmenopausal osteoporosis, which can specifically detect the expression level of the miR-338 cluster in tissues, and is used for non-invasive and early auxiliary diagnosis of postmenopausal osteoporosis in clinic. In addition, inhibitors of the miR-338 cluster have the efficacy of promoting osteogenesis and can be used for treating or preventing postmenopausal osteoporosis.

4 Claims, 12 Drawing Sheets

MIRNA MARKER AND KIT ASSOCIATED WITH POSTMENOPAUSAL OSTEOPOROSIS

CROSS-REFERENCE TO RELATED APPLICATION(S)

The present application claims priority to International Application No. PCT/CN2017/100135 filed on Sep. 1, 2017 which claims the priority of Chinese Patent Application No. 201710708188.9, filed before the CNIPA on Aug. 17, 2017, entitled "MIRNA MARKER AND KIT ASSOCIATED WITH POSTMENOPAUSAL OSTEOPOROSIS", which is herein incorporated by reference in its entirety.

TECHNICAL FIELD

The present invention relates to the field of genetic engineering, more particularly, to a miRNA marker and a kit associated with postmenopausal osteoporosis.

BACKGROUND ART

MicroRNAs (miRNAs) represent specific micromolecular non-coding RNAs that regulate gene expression after transcription. A single miRNA can interact with transcription factors by inhibiting the expression of a series of related functional genes. To date, a plurality of studies have demonstrated that blocking miRNA can block the progression of osteoporosis. Multiple independent experiments on animal models have also verified that many miRNAs have altered expression during osteoporosis and are involved in the pathological process of osteoporosis. Since the first discovery of miRNA in 1993, miRNA has received more and more attention from researchers. The role of miRNAs in the occurrence and development of various diseases has also been extensively and deeply explored in recent years. More than 2000 miRNAs in humans have been reported to be tissue or cell specific. More and more studies have shown that there are stably expressed miRNAs in human body fluids such as urine, sweat, saliva and the like, especially miRNAs in serum or plasma. MicroRNAs can be stably, replicably and persistently present in serum or plasma, thus making it possible to use miRNAs for diagnosis or treatment of a variety of diseases, including osteoporosis. The diagnosis of osteoporosis by analyzing the expression of miRNAs in peripheral blood is non-invasive, stable, and real-time.

Multiple disease-related target genes of any miRNA can be searched through the bioinformatics technology and experimental means, and the development of technologies for chemical synthesis of oligonucleotide allows to directly inhibit the expression of some specific miRNAs, the oligonucleotide freely shuttles between cells, and specifically binds to the specific miRNAs by complementary base pairing, thereby blocking the function of the miRNAs. Therefore, unlike transcription factors, specific miRNAs are more liable to be specifically targeted by oligonucleotides in humans and animals.

Osteoporosis is a metabolic bone lesion with reduced bone mass, destruction of bone tissue microstructure, increased bone fragility, and increased incidence of fractures. Postmenopausal osteoporosis is a disease with high incidence in postmenopausal women, and is a multifactorial disease. Estrogen deficiency, genetic factors, nutritional status, lifestyle habits, physical exercise, menstrual cycle disorders, menopause earlier than 40 years old and the like are related to the pathogenesis, but postmenopausal estrogen deficiency is an important cause of postmenopausal osteoporosis. In postmenopausal women, bone loss in the first 5 to 7 years increases at a rate of 1% to 5% per year.

At present, the determination of bone mineral density by dual-energy X-ray absorption technique is the gold standard for early detection and diagnosis of osteoporosis, and the bone metabolism can also be reflected by measuring biochemical indicators of bone metabolism such as BAP, OC, Tracp5b, PINP, NTX, CTX and the like. Bone mineral density test can predict bone mineral density in normal, low, and osteoporotic conditions, and predict the risk of certain fractures. However, the process of osteoporosis is very slow, and the change is not obvious in a short time, it needs a long time to observe and perform detection continuously, and once bone loss is found, it is difficult to reverse the reduced bone mineral density, which brings great difficulties to the early diagnosis of patients in clinic.

SUMMARY OF THE INVENTION

One purpose of the present invention is to provide the use of miR-338 cluster as a marker of postmenopausal osteoporosis.

Wherein, the miRNA cluster refers to two or more clustered miRNAs that are close in distance on genome (usually less than 2 kb).

Figure 1:
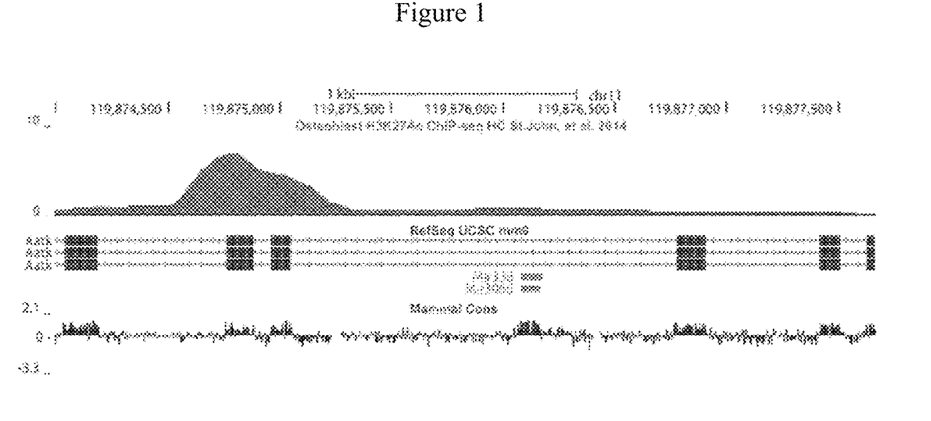
FIG. 1 is a diagram showing the positional relationship of encoding genes of miR-338-3p and miR-3065-5p according to a preferred embodiment of the present invention.

In the present invention, the miR-338 cluster is miRNAs that are close in distance on genome (less than 2 kb) to the genome encoding miR-338, both miR-338-3p and miR-3065-5p belong to the miR-338 cluster, and the positional relationship of the encoding gene of miR-338-3p and miR-3065-5p is shown in FIG. 1.

Wherein, the miR-338 cluster is preferably miR-338-3p and/or miR-3065-5p.

The postmenopausal osteoporosis is early postmenopausal osteoporosis, i.e., osteoporosis with a detected T value between −2.5 and −1.

For example, the existing osteoporosis imaging assay only can detect osteoporosis 12 weeks after osteoporosis occurs, while the miR-338 cluster of the present invention can be used to detect early postmenopausal osteoporosis, for example, 8 weeks after osteoporosis occurs, preferably 1 week after osteoporosis occurs. That is, osteoporosis can be clearly detected within 8 weeks, preferably within 1 week after osteoporosis occurs by using the miRNA cluster of the present invention.

In the present invention, the expression levels of the miR-338 cluster such as miR-338-3p and miR-3065-5p in the serum of patients with early postmenopausal osteoporosis are detected, and the results show that the expression level of the miR-338 cluster is significantly higher than that of the control healthy group. At the same time, the results of ROC analysis show that the miR-338 cluster has a high diagnostic value.

When the miR-338 cluster is miR-338-3p and miR-3065-5p, it is more effective as a marker of postmenopausal osteoporosis.

The present invention also provides the use of a biomaterial containing miR-338 cluster as a marker of postmenopausal osteoporosis.

Wherein, the miR-338 cluster is preferably miR-338-3p and/or miR-3065-5p.

Preferably, the biomaterial may be one or more of a vector, a host cell, a transgenic cell line, and an engineering bacteria.

The present invention also provides the use of the miR-338 cluster in the preparation of an auxiliary diagnostic kit for postmenopausal osteoporosis.

Wherein, the miR-338 cluster is highly expressed in the serum of patients with postmenopausal osteoporosis. "Highly expressed" and "significant" as used in the present invention mean that the p value is generally less than 0.05 in a statistical sense.

Wherein, the miR-338 cluster is preferably miR-338-3p and/or miR-3065-5p.

With the diagnostic kit of the present invention, it is only necessary to measure the content of the miR-338 cluster in the serum of the patient, and as compared with the previous diagnostic method, the advantages are that the diagnosis with the kit is non-invasive and sensitive, and the postmenopausal osteoporosis can be diagnosed when the patient suffers from the early stage of postmenopausal osteoporosis, and preferably, the postmenopausal osteoporosis can be diagnosed when the patient suffers from early postmenopausal osteoporosis, i.e., osteoporosis with a T value between −2.5 and −1.

The present invention also provides the use of an inhibitor of miR-338 cluster, such as miR-338-3p and/or miR-3065-5p, in the preparation of a drug for treating or preventing postmenopausal osteoporosis.

Wherein, a drug for treating or preventing postmenopausal osteoporosis is a drug for promoting osteogenic differentiation.

The present invention also provides a drug for treating or preventing postmenopausal osteoporosis, which comprises an inhibitor of miR-338 cluster, preferably an inhibitor of miR-338-3p and/or miR-3065-5p.

In the present invention, it was unexpectedly found that the miR-338 cluster, preferably miR-338-3p and/or miR-3065-5p, is highly expressed in patients with postmenopausal osteoporosis, can be used as a marker of postmenopausal osteoporosis, and can be used for the preparation of an auxiliary diagnostic kit for postmenopausal osteoporosis, the expression level of the miR-338 cluster, preferably miR-338-3p and/or miR-3065-5p, in the serum of tissues can be specifically detected, the auxiliary diagnostic kit can be used timely and effectively for early auxiliary diagnosis of clinical postmenopausal osteoporosis, and the above diagnosis can be achieved with serum without the need for additional wounds. The present invention also finds that the inhibitor of the miR-338 cluster can effectively block the progression of osteoporosis and promote osteogenesis, thereby effectively treating or preventing postmenopausal osteoporosis, and the inhibitor of the miR-338 cluster can be used as a drug for treating or preventing postmenopausal osteoporosis, which has good clinical application value and broad application prospects.

SPECIFIC MODES FOR CARRYING OUT THE EMBODIMENTS

The present invention will be further described in detail below in conjunction with specific Examples. The following Examples are intended to illustrate the present invention but are not intended to limit the scope of the present invention.

The technical means used in the Examples are conventional techniques well known to a person skilled in the art unless otherwise specified. The reagents used in the Examples were commercially available unless otherwise specified.

Example 1

Experimental procedure: Blood samples from 15 patients with postmenopausal osteoporosis and 15 healthy samples were collected, serum was collected after centrifugation, and total RNA (including miRNA) in serum was extracted using a kit, RT-PCR was performed after reverse transcription, and statistical analysis was performed according to CT values.

Figure 2A:
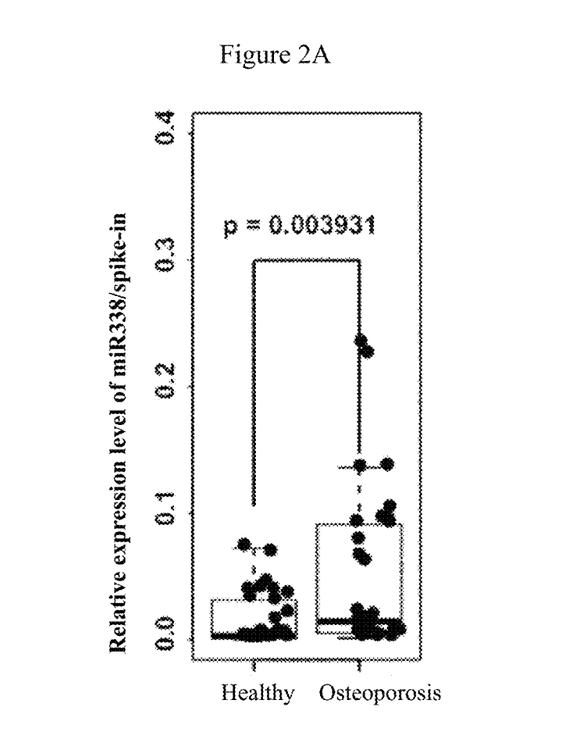
FIG. 2A is a graph showing the contents of miR-338-3p in a postmenopausal osteoporosis patient group and a healthy group according to Example 1 of the present invention.
Figure 2B:
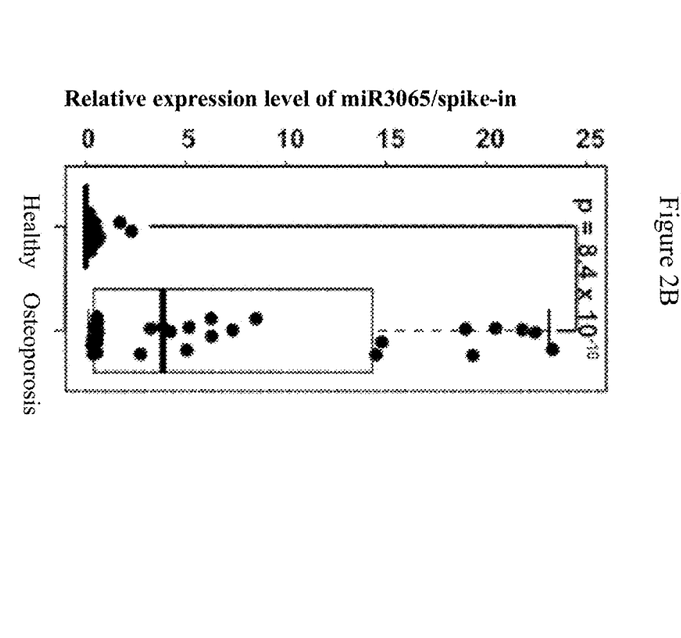
FIG. 2B is a graph showing the contents of miR-3065-5p in a postmenopausal osteoporosis patient group and a healthy group according to Example 1 of the present invention.
Figure 2C:
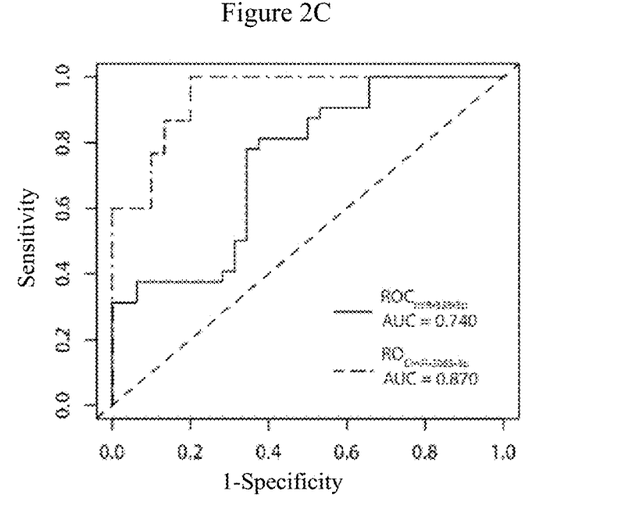
FIG. 2C is a diagram showing the ROC curve of miR-338-3p and miR-3065-5p in Example 1 according to the present invention.

The expression levels of miR-338-3p and miR-3065-5p in the blood of patients with postmenopausal osteoporosis were detected, as shown in FIGS. 2A and 2B, and the results showed the expression levels of miR-338-3p and miR-3065-5p were significantly higher than that of the control healthy group sample, wherein, each black dot represents each sample, and the higher the position of the dots, the more the content. At the same time, as shown in FIG. 2C, the results of ROC analysis showed that miR-338-3p and miR-3065-5p have relative high diagnostic value.

Establishment of an osteoporosis model of a mouse subjected to bilateral ovarian ablation: The mice were fixed in the prone position, an outwardly inclined incision of about 1 cm in length was made with ophthalmic scissors on the back at both sides of the spine, the skin and muscle layers were peeled off to find the ovarian tissue, and ovary was removed after the ovarian mesangial vessels were ligated with a 4th wire. The skin was sutured. The other ovary was removed using the same method; and the skin was sutured after repositioning of the uterus.

Figure 3A:
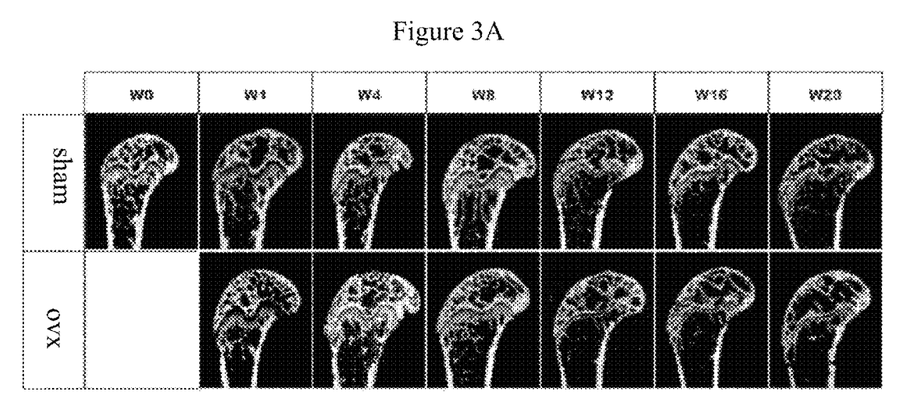
FIG. 3A is a micro-CT image of femurs of a mouse at 0, 1, 4, 8, 12, 16 and 18 weeks after bilateral ovarian ablation and a control group (Sham group: untreated group) according to Example 1 of the present invention.
Figure 3B:
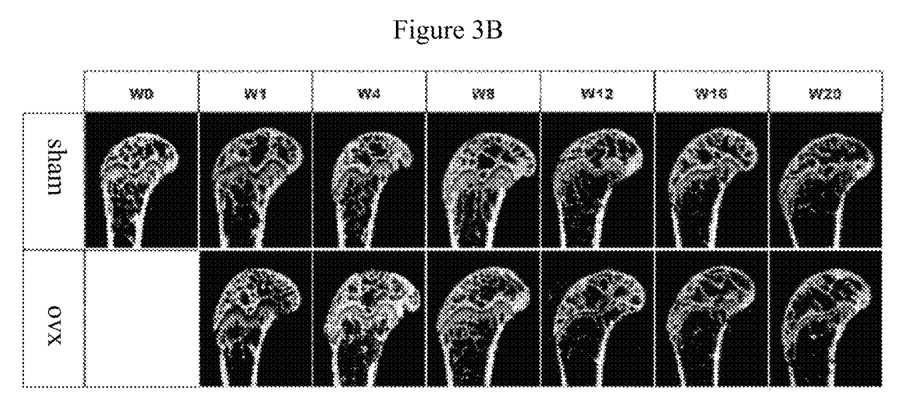
FIG. 3B is a staining diagram of HE stained femur sections of a mouse at 0, 1, 4, 8, 12, 16 and 18 weeks after bilateral ovarian ablation and a control group (Sham group: untreated group) according to Example 1 of the present invention.
Figure 3C:
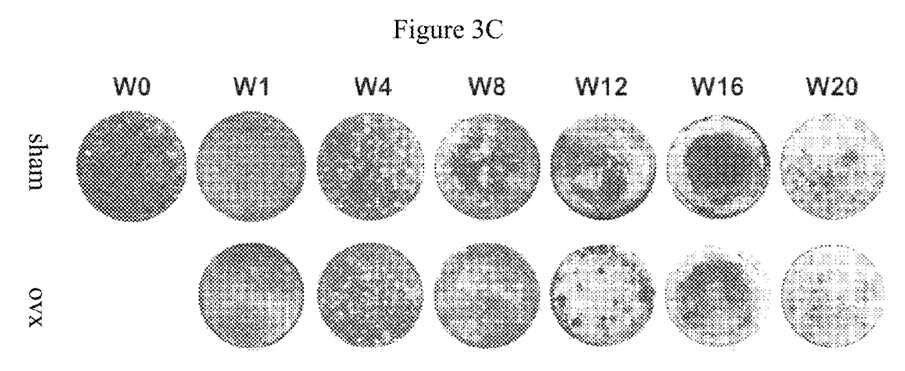
FIG. 3C is a staining diagram of femoral bone marrow mesenchymal stem cells of a mouse at 0, 1, 4, 8, 12, 16 and 18 weeks after bilateral ovarian ablation and a control group (Sham group: untreated group), wherein the bone marrow mesenchymal stem cells were subjected to alizarin red staining 14 days after mineralization induction.
Figure 4A:
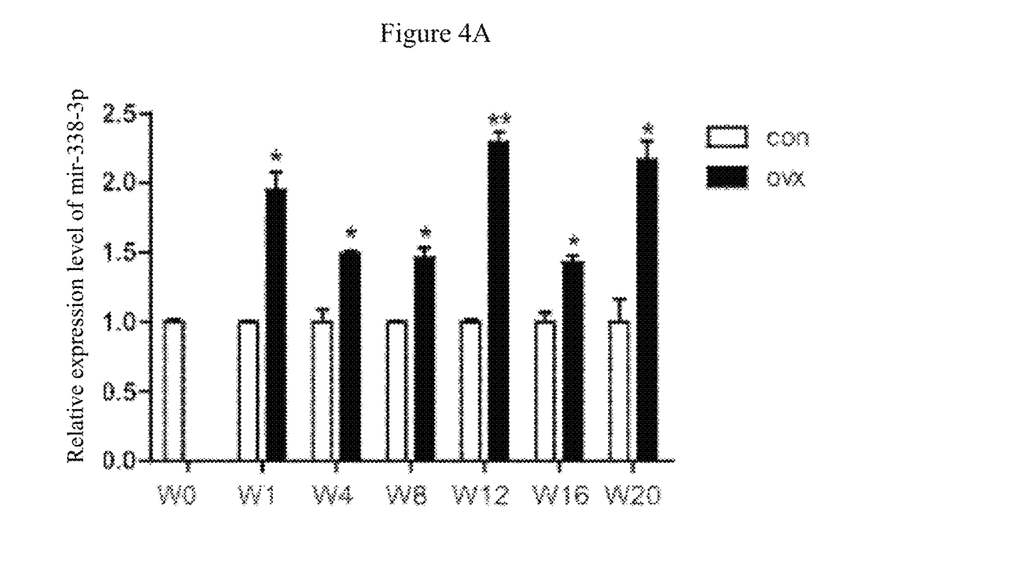
FIG. 4A is a graph showing the expression level of miR-338-3p versus the time after OVX (ovariectomized) according to Example 1 of the present invention.
Figure 4B:
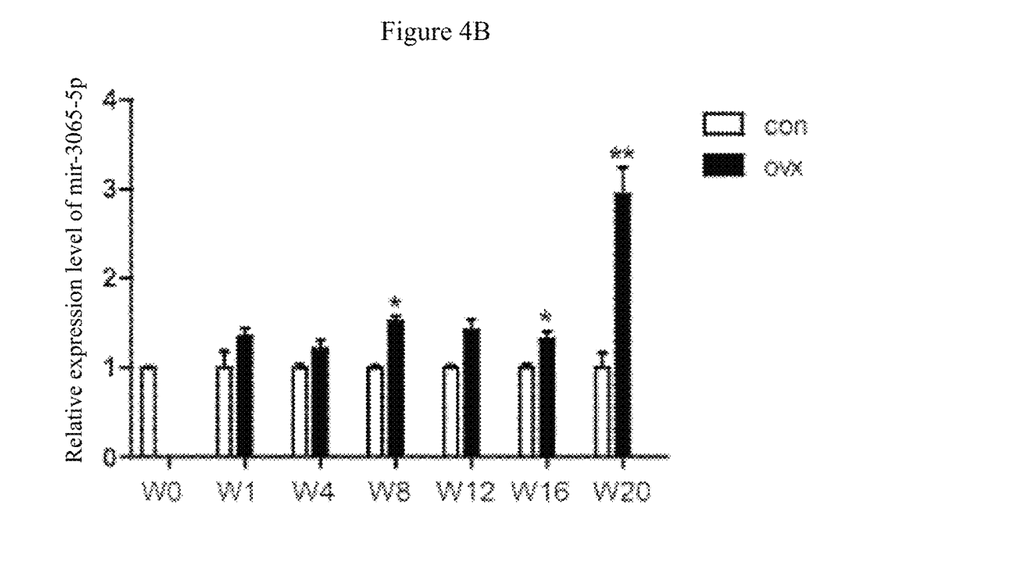
FIG. 4B is a graph showing the expression level of miR-3065-5p versus the time after OVX according to Example 1 of the present invention.

The results of micro-CT and HE staining of the mouse femur showed that, as shown in FIGS. 3A and 3B, a significant reduction in bone mass was observed 3 months after OVX, while bone mass in the OVX group was lower than that in the CON group. As shown in FIG. 3A, the trabecular bone density was higher at 0 to 8 weeks, and there was no difference between the Sham group and the OVX group. By the 12$^{th}$ week after surgery, the number of trabecular bone in the OVX group was significantly lower than that in the sham group. Then, as time goes on after surgery, the trabecular bone density gradually decreased, and the trabecular bone density of the OVX group was lower than that of the sham group. FIG. 3C shows that the mineralization ability of BMSCs (bone marrow mesenchymal stem cells) of mouse femurs decreases significantly from the third month after OVX, and the mineralization ability of the OVX was lower than that of the CON group. At the same time, it was found that the expression levels of miR-338-3p and miR-3065-5p in the serum of mice increased as time goes on after OVX. It is worth noting that the expression level of miR-338-3p was significantly higher than that of the control group one week after OVX, the expression level of miR-3065-5p was significantly higher than that of the control group eight weeks after OVX, significantly earlier than the imaging test (micro-CT), as shown in FIGS. 4A and 4B. This indicated that miR-338-3p and miR-3065-5p can be used as early diagnostic marker of postmenopausal osteoporosis.

Figure 5A:
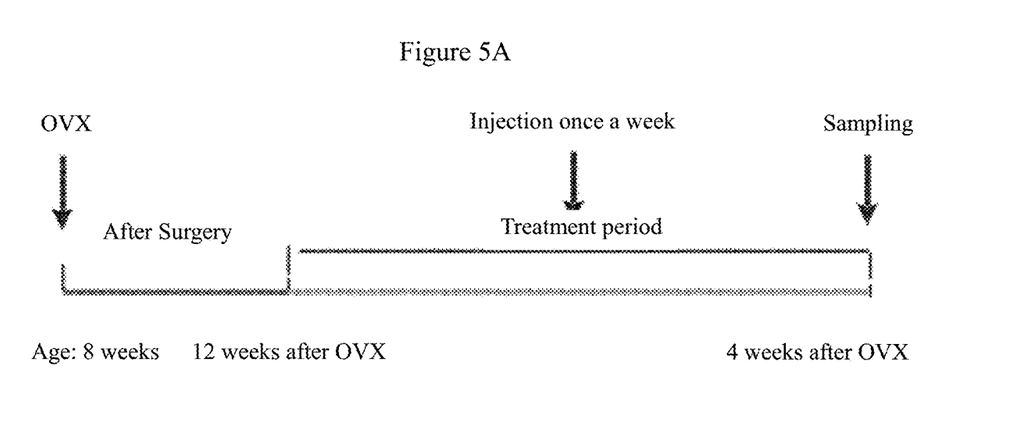
FIG. 5A is a flow chart of an experimental scheme for injecting an inhibitor according to Example 1 of the present invention.

Three months after OVX, inhibitors of miR-338-3p and miR-3065-5p were respectively injected into mice by tail vein injection, once a week (a total of 4 injections), and the flow chart thereof was shown in FIG. 5A. Specifically, bilateral ovarian ablation was performed on 8-week-old Balb/c mice, and the inhibitor of miR-338-3p or miR-3065-5p was injected through the tail vein three months after surgery, once a week for one month (a total of 4 injections), and then the specimen was collected.

Figure 5B:
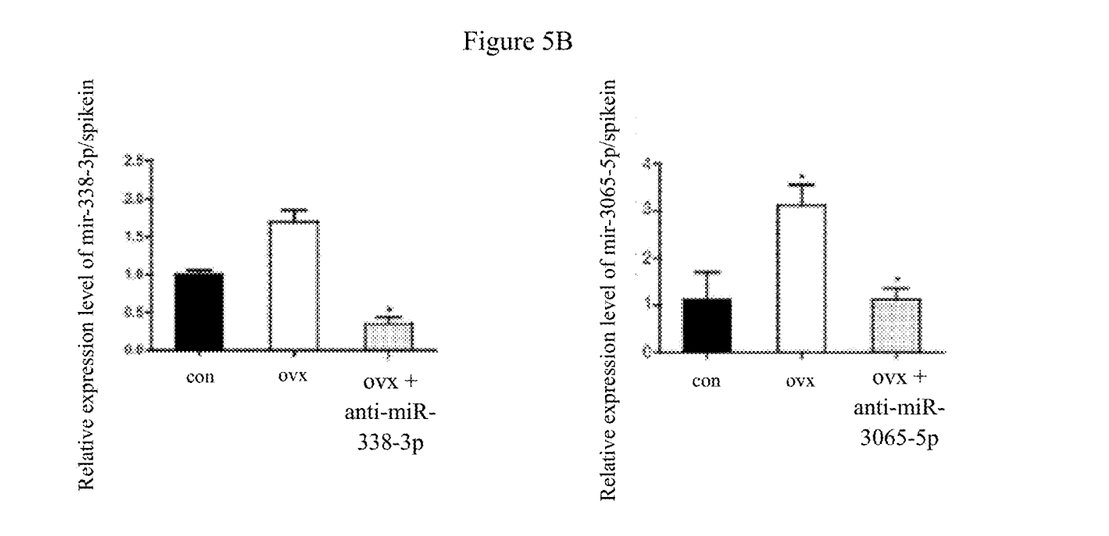
FIG. 5B is a graph showing the expression levels of miR-338-3p or miR-3065-5p in mouse serum after injection of miR-338-3p or miR-3065-5p inhibitor according to Example 1 of the present invention; the black column is the untreated control (con) group, the white column is the OVX group 3 months after ovarian ablation, and the gray column is the group in which the inhibitor was injected after OVX.
Figure 5C:
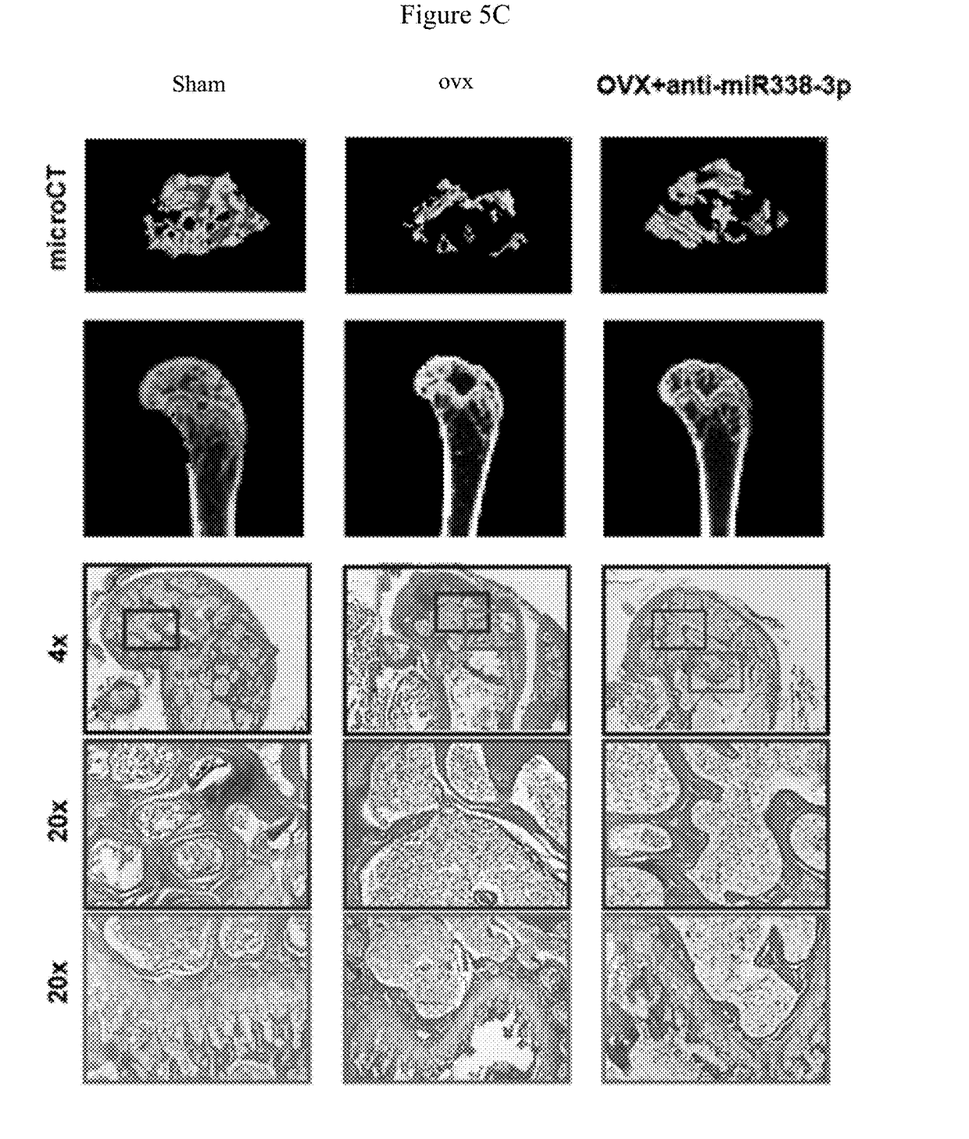
FIG. 5C is a diagram showing the micro-CT analysis of a femur, a three-dimensional reconstruction map of a trabecular bone and a HE staining map for a mouse after injection of a miR-338-3p inhibitor according to Example 1 of the present invention.
Figure 5D:
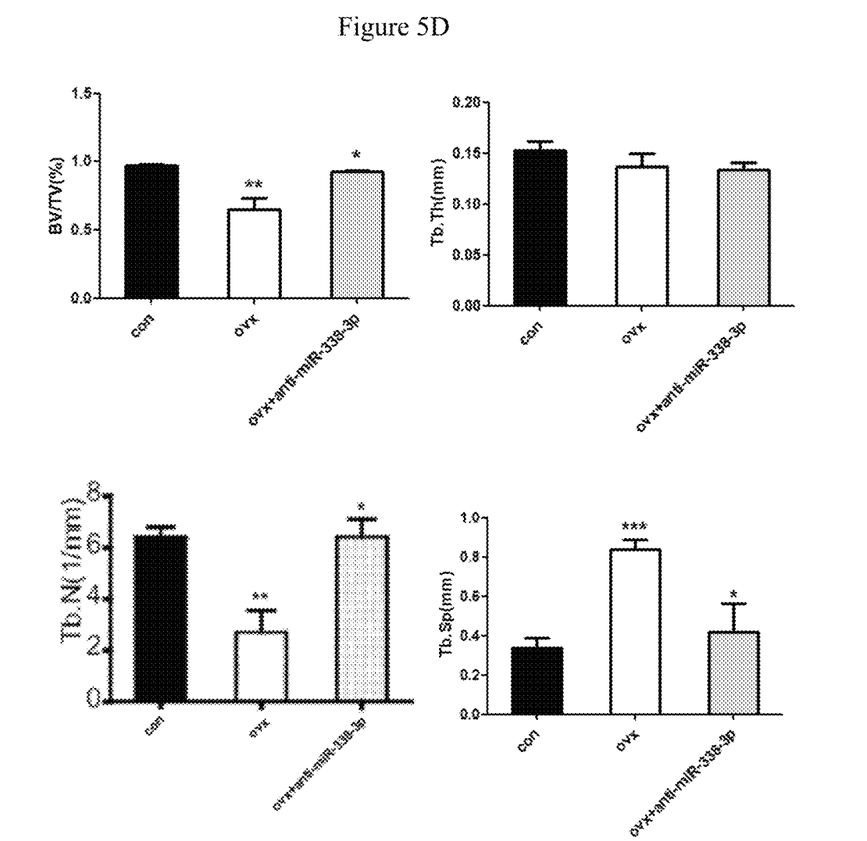
FIG. 5D is a graph showing trabecular bone volume ratio, trabecular bone thickness, number of trabecular bone per unit volume, and trabecular bone spacing in the reconstructed trabecular bone of FIG. 5C in the OVX, con, and OVX+anti-miR-338-3p groups.
Figure 5E:
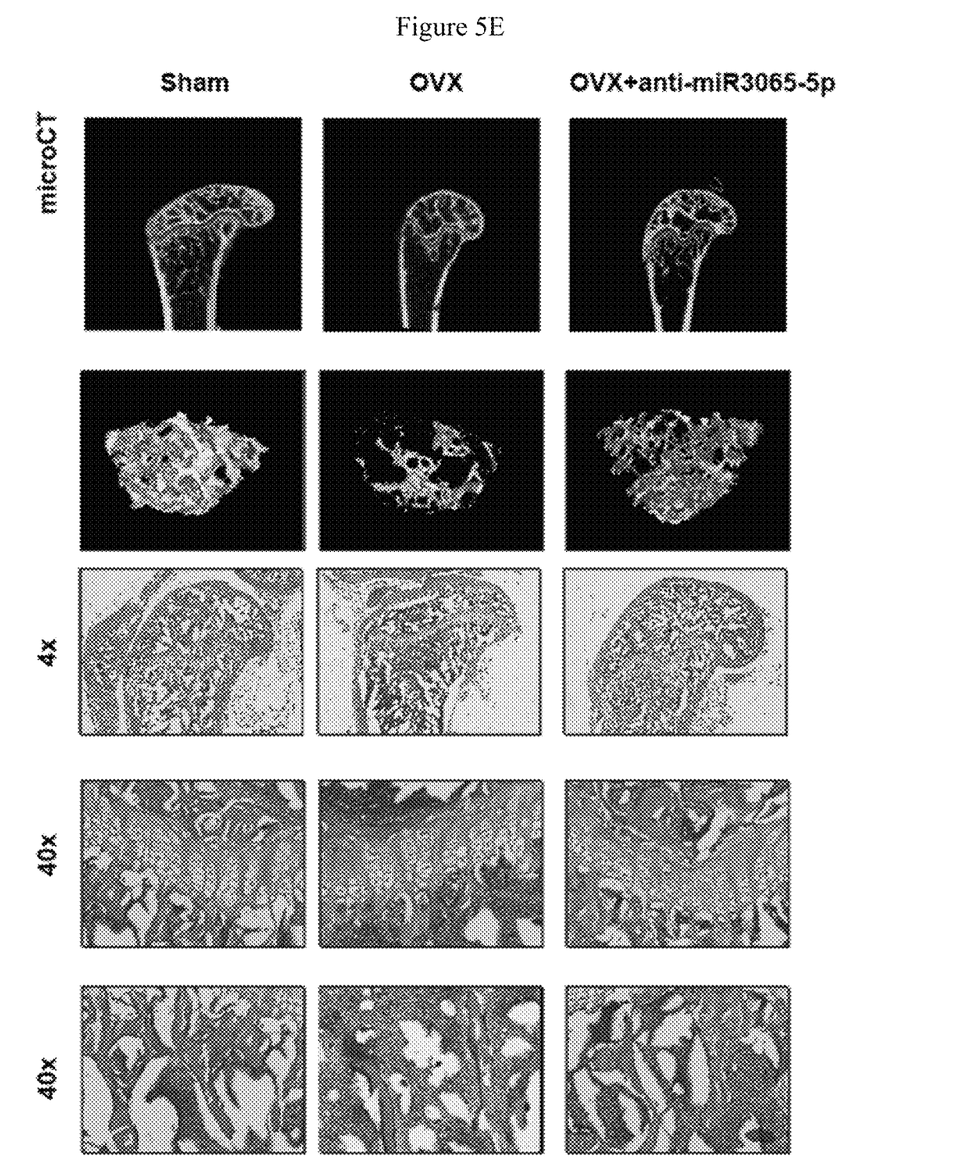
FIG. 5E is a diagram showing the micro-CT analysis of a femur, a three-dimensional reconstruction map of a trabecular bone and a HE staining map for a mouse after injection of a miR-3065-5p inhibitor according to Example 1 of the present invention.
Figure 5F:
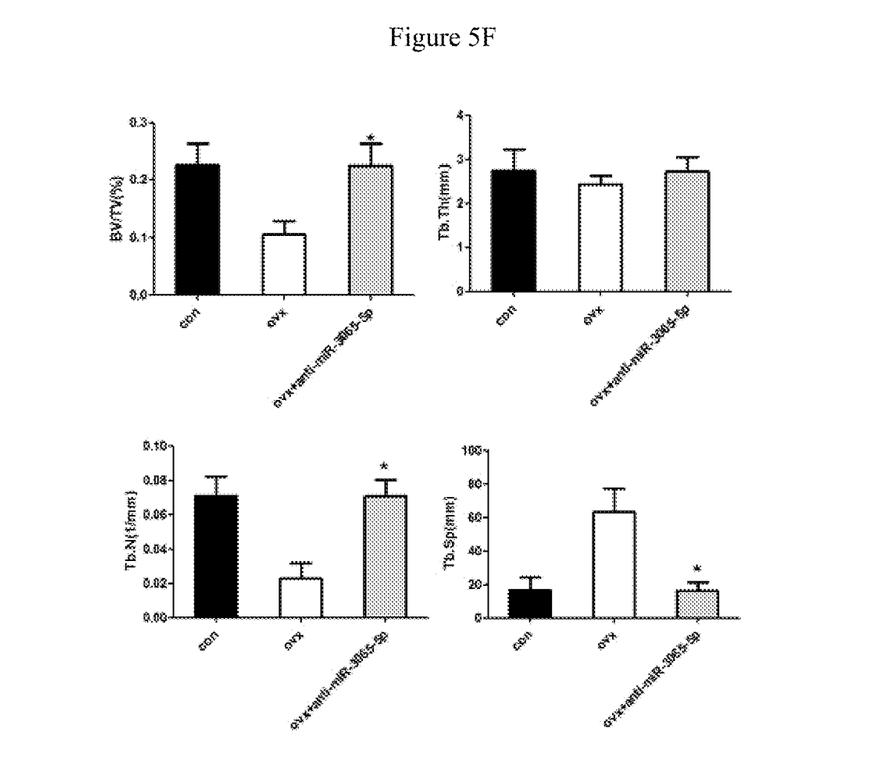
FIG. 5F is a graph showing trabecular bone volume ratio, trabecular bone thickness, number of trabecular bone per unit volume, and trabecular bone spacing in in the reconstructed trabecular bone of FIG. 5E in the OVX, con, and OVX+anti-miR-3065-5p groups.

The contents of miR-338-3p and miR-3065-5p in blood and femur bone marrow mesenchymal stem cells were detected. The results showed that the contents of miR-338-3p and miR-3065-5p in the OVX group were significantly higher than that in the control group, the content of miRNA decreased significantly after injection of the inhibitor, as shown in FIG. 5B. As shown in FIGS. 5C and 5E, the results of microCT and staining showed that the trabecular bone and bone mineral density of the inhibitor group were significantly higher than those of the OVX group, indicating that inhibition of miR-338-3p and miR-3065-5p can block the progression of osteoporosis, and has obvious therapeutic effects on postmenopausal osteoporosis. As shown in FIGS. 5D and 5F, BV/TV (%), Tb.Th (mm) and Tb.N (1/mm) of the OVX group are lower than those of the con group, and BV/TV (%), Tb.Th (mm) and Tb.N (1/mm) of OVX+anti-miR-338-3p group and OVX+anti-miR-3065-3p group are higher than those of the OVX group. Tb.Sp (mm) of the OVX group is higher than that of the con group, and Tb.Sp (mm) of the OVX+anti-miR-338-3p group and the OVX+anti-miR-3065-3p group is lower than that of the OVX group. These results further support the results of micro-CT and HE staining.

Figure 6A:
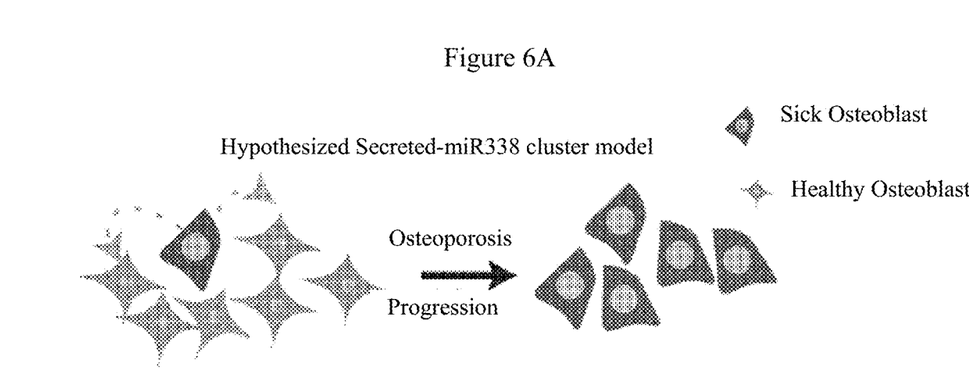
FIG. 6A shows an experimental hypothesis pattern diagram established in Example 1 of the present invention using gene editing means of crispr-cas9 showing that miR-338-3p and miR-3065-5p in healthy cells are from miR-338-3p and miR-3065-5p that are highly expressed in unhealthy cells; wherein, stellate cells represent healthy osteoblasts, and square cells represent unhealthy osteoblasts.

As shown in FIG. 6A, experimental hypothesis pattern diagram established using the gene editing means of cristr-cas9 showing miR-338-3p and miR-3065-5p in healthy cells are from miR-338-3p and miR-3065-5p that are highly expressed in unhealthy cells (miR-338-3p and miR-3065-5p in healthy cells are from miR-338-3p and miR-3065-5p which are highly expressed in unhealthy cells). The osteoblast cell lines with mR-338-3p and miR-3065-5p knocked out were established using the gene editing means of cristr-cas9, which were used to represent healthy osteoblasts, and the wild-type mc3T3-E1 represented unhealthy osteoblast.

Figure 6B:
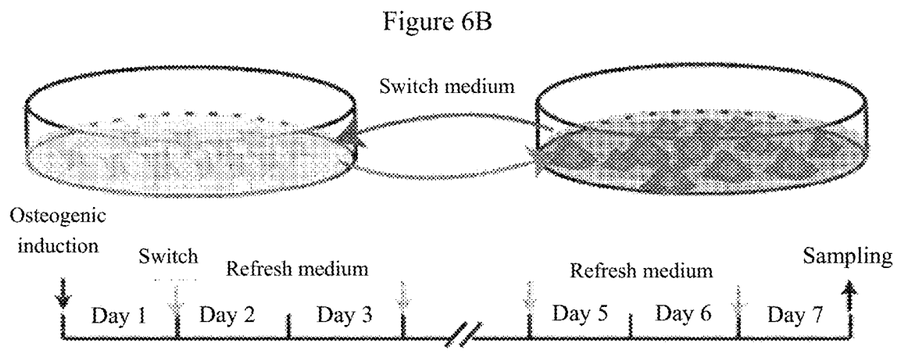
FIG. 6B is a flow chart showing the culture and induction of a cell line with knockout miR-338-3p/miR-3065-5p and a wild-type osteoblast cell line according to Example 1 of the present invention.
Figure 6C:
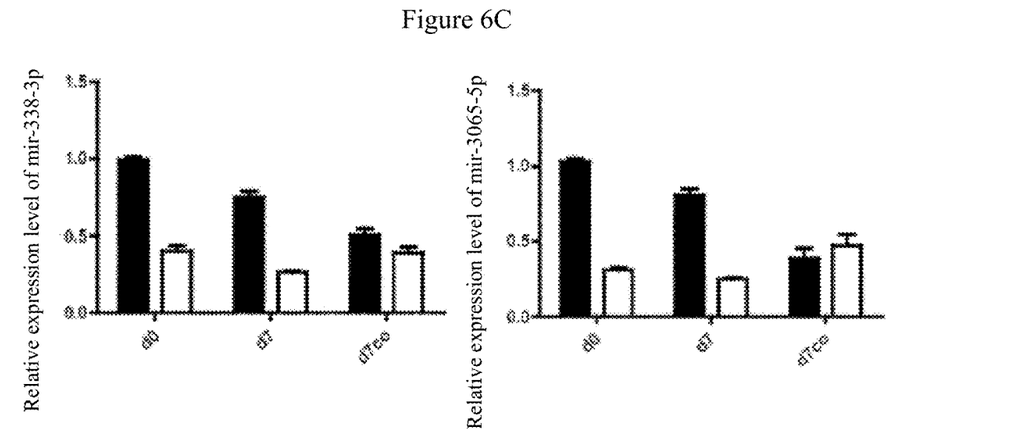
FIG. 6C is a comparison chart of expression levels of miR-338-3p and miR-3065 in the supernatants of the WT group (the wild-type osteoblast cell line group) and the 3065ko group (the cell line with miR-338-3p/miR-3065-5p knocked out) according to Example 1 of the present invention; wherein the black column represents the WT group, and the white column represents the 3065ko group.
Figure 6D:
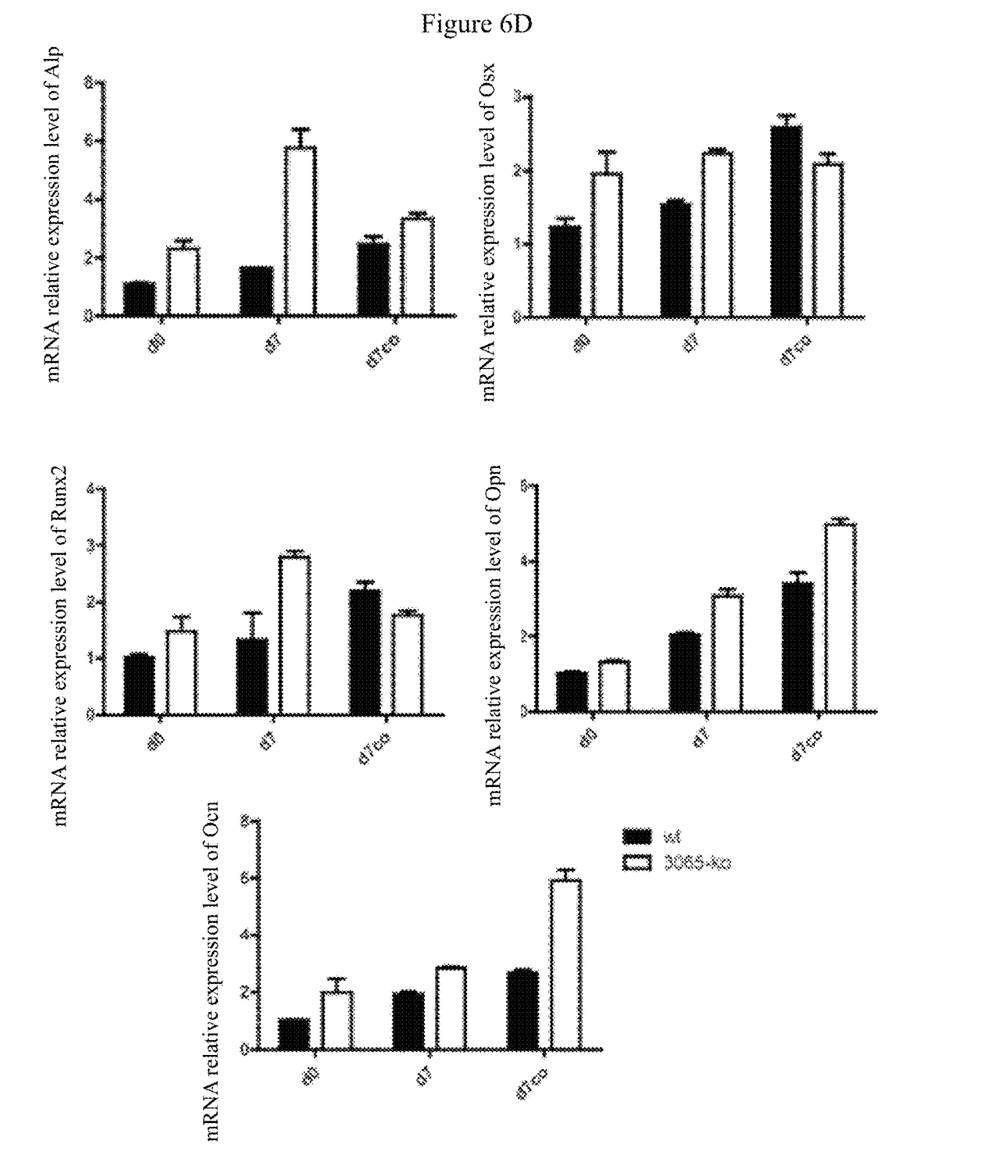
FIG. 6D is a comparison chart of expression levels of Alp, Ocn, Opn, Alp and Runx2 of the WT group (the wild-type osteoblast cell line group) and the 3065ko group (the cell line with miR-338-3p/miR-3065-5p knocked out) according to Example 1 of the present invention; wherein the black column represents the WT group, and the white column represents the 3065ko group.

The cell supernatants were extracted 0, 3 and 7 days after induction of differentiation of wild-type osteoblasts, and the expression levels of miR-338-3p and miR-3065-5p in the supernatant showed a downward trend, which is consistent with the expression trend thereof during osteoblast differentiation. Subsequently, we induced the cell line with miR-338-3p/miR-3065-5p knocked out and the wild-type osteoblast cell line, respectively, and the culture supernatants were switched every two days. Seven days later, the supernatants of two cell lines were collected and assayed for the content of miRNA, as shown in FIGS. 6C and 6D. Wherein, in FIG. 6C, D0 represents mineralization for 0 day, d7 represents culture with mineralization inducing solution for 7 days, and d7co represents culture according to the culture method in FIG. 6B for 7 days. The results showed that on D0 day of the mineralization, the content of miR-338-3p in the WT group was significantly higher than that in the 3065ko group, and the difference was increased on 7 day of mineralization. After 7 days of culture with the switched medium, this difference was reduced.

The osteogenic ability of the WT group (wild-type osteoblast cell line group) and the 3065ko group (cell line with miR-338-3p/miR-3065-5p knocked out) was examined in FIG. 6D. The effects of the change of the contents of miR-338-3p/miR-3065-5p on osteogenic ability were examined by detecting the expression levels of Alp, Ocn, Opn, Alp and Runx2 of different groups. Consistent with the results in FIG. 6C, on d0 day of the mineralization, the expression level of osteogenic gene of the WT group was lower than that of the 3065ko group due to the high expression of miR-338-3p/miR-3065-5p in the WT group, and the difference increased in the d7 group, and after 7 days of mineralization induction with the switched medium, the expression level of osteogenic gene was down-regulated in the 3065ko group due to the effect of the high expression of miR-338-3p/miR-3065-5p in the medium of the 3wt group, and the difference between the 3065ko group and the wt group was decreased. The above results showed that the expression levels of highly expressed miR-338-3p and miR-3065-5p in wild-type were decreased after co-culture with the supernatant of cell line with miR-338-3p/miR-3065-5p knocked out, and the expression levels of the lowly expressed miR-338-3p and miR-3065-5p in cell line with miR-338-3p/miR-3065-5p knocked out were increased after co-culture with the supernatant of wild-type osteoblast cell line. This conclusion also verifies the experimental hypothesis of FIG. 6B.

Figure 7:
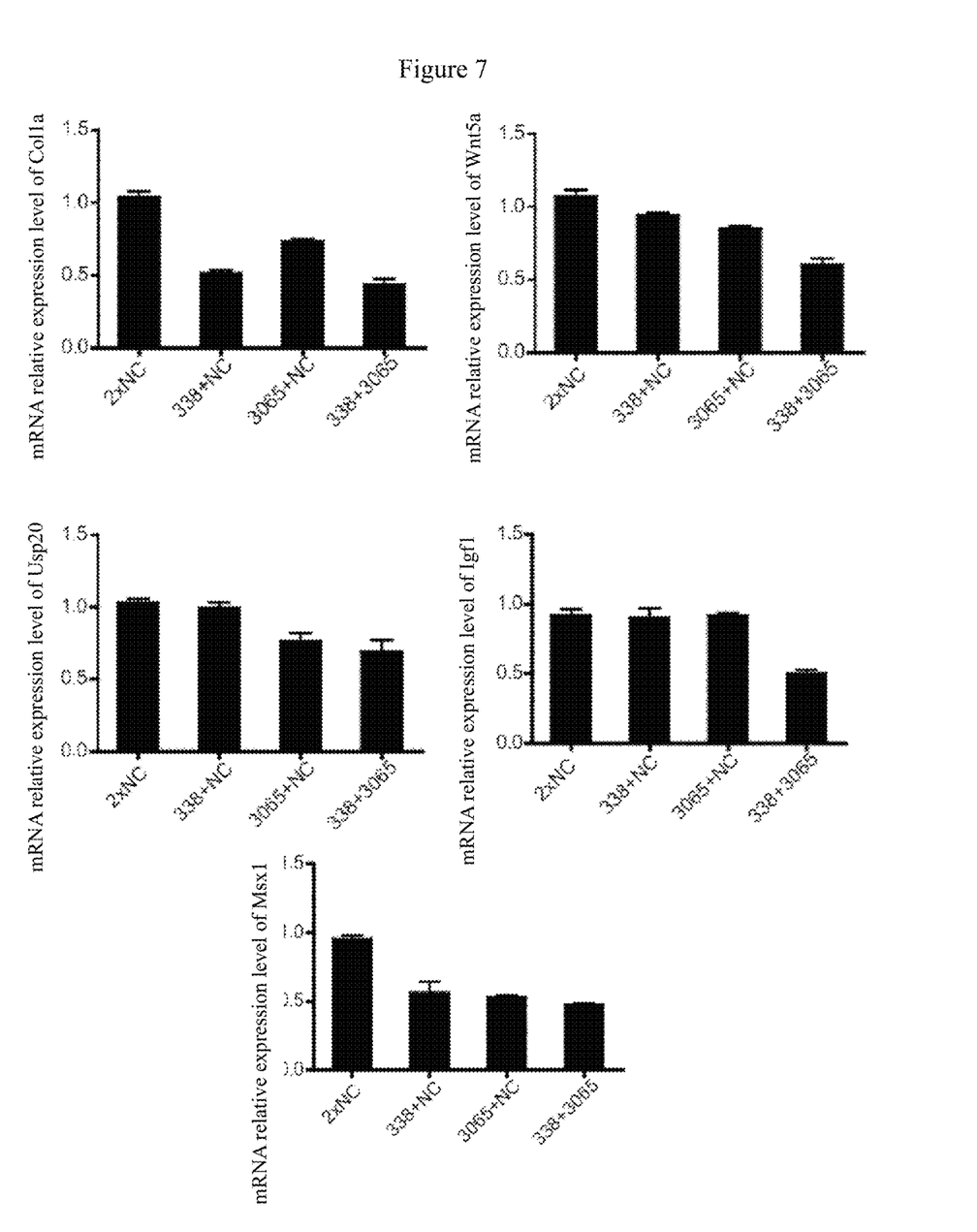
FIG. 7 is a comparison chart of expression levels of downstream genes Col1a, Wnt5a, usp20, Igf1 and Msx1 when miR-338-3p and miR-3065-5p were overexpressed respectively, and miR-338 and miR-3065 were overexpressed simultaneously in mc3T3 in Example 1 according to the present invention.

At the same time, miR-338-3p or miR-3065-5p was overexpressed respectively, and miR-338 and miR-3065 were overexpressed simultaneously in mc3T3, and the expression levels of the downstream genes Col1a, Wnt5a, usp20, Igf1 and Msx1 (which are genes positively associated with osteogenic differentiation) were detected. The results showed that, as shown in FIG. 7, overexpression of miR-338-3p or miR-3065-5p, and simultaneous overexpression of miR-338 and miR-3065 can significantly down-regulate the expression of downstream genes. At the same time, the down-regulation of downstream genes by overexpression of miR-338-3p and miR-3065-5p was significantly greater than that caused by overexpression of miR-338-3p or miR-3065-5p alone, indicating that simultaneous use of inhibitors of miR-338-3p and miR-3065-5p has synergistic effect, and can promote osteogenic differentiation, thereby treating or preventing postmenopausal osteoporosis better.

In normal women, estrogen has a relatively high normal level, which lead to the rise of Runx2 levels. Runx2 acts as an upstream gene of miR-338-3p and miR-3065-5p genes, can decrease the expression levels of miR-338-3p and miR-3065-5p. Meanwhile, Runx2 acts as a downstream target gene of miR-338-3p and miR-3065-5p. A small amount of miR-338-3p and miR-3065-5p bind with the 3'UTR region of their downstream Runx2, resulting in higher expression level of Runx2. Then more Runx2 binds to the promoter regions of miR-338-3p and miR-3065-5p to inhibit the expression of miR-338-3p and miR-3065-5p, allowing miR-338-3p and miR-3065-5p to maintain a relative low expression level in peripheral blood. In patients with postmenopausal osteoporosis, estrogen levels drop dramatically, resulting in a decrease in Runx2 level. Less Runx2 binds to the promoter regions of miR-338-3p and miR-3065-5p, promoting the expression of miR-338-3p and miR-3065-5p. Then more miR-338-3p and miR-3065-5p will bind to their downstream gene Runx2, causing further decrease in Runx2 level and thereby resulting in fewer Runx2 binding in the promoter region of miR-338-3p and miR-3065-5p and allowing miR-338-3p and miR-3065-5p to maintain a relative high expression level in peripheral blood.

The above is only the preferred embodiment of the present invention, and is not intended to limit the present invention. Any modifications, equivalent substitutions, improvements and the like, made within the spirit and scope of the present invention, are intended to be included within the scope of the present invention.

INDUSTRIAL APPLICABILITY

The present invention provides a miRNA marker and a kit associated with postmenopausal osteoporosis, and in particular to the use of the miR-338 cluster as a marker of postmenopausal osteoporosis. In the present invention, it was found that miR-338 cluster such as miR-338-3p and/or miR-3065-5p are highly expressed in patients with postmenopausal osteoporosis, and it can be used as a marker of postmenopausal osteoporosis, used for preparing an auxiliary diagnostic kit for postmenopausal osteoporosis, which can specifically detect the expression level of the miR-338 cluster in tissues, and can be timely and effectively used for non-invasive and early auxiliary diagnosis of postmenopausal osteoporosis in clinic. In addition, the inhibitors of the miR-338 cluster have the efficacy of promoting osteogenesis, and can effectively treat or prevent postmenopausal osteoporosis. The marker provided by the present invention can be applied to the field of postmenopausal osteoporosis detection on a large scale, and is suitable for industrial application, and has broad market prospects.

What is claimed is:

1. A method for diagnostic detection of postmenopausal osteoporosis using a miR-3065-5p, the method comprising:
   obtaining serum from a subject;
   determining expression level of miR-3065-5p in the serum, and
   preventing postmenopausal osteoporosis by administering a drug containing an inhibitor of miR-3065-5p, wherein the measured expression level of miR-3065-5p is higher than a control.

2. The method of claim 1, wherein the serum is obtained less than 12 weeks after onset of postmenopausal osteoporosis.

3. The method of claim 2, wherein the serum is obtained less than 8 weeks after onset of postmenopausal osteoporosis.

4. The method of claim 3, wherein the serum is obtained less than 1 week after onset of postmenopausal osteoporosis.

* * * * *